US012746031B2

(12) United States Patent
Kaloostian

(10) Patent No.: US 12,746,031 B2
(45) Date of Patent: Sep. 29, 2026

(54) SURGICAL APPARATUS

(71) Applicant: LINUS VENTURES LLC, Pasadena, CA (US)

(72) Inventor: Paul Kaloostian, Pasadena, CA (US)

(73) Assignee: LINUS VENTURES LLC, Pasadena, CA (US)

( * ) Notice: Subject to any disclaimer, the term of this patent is extended or adjusted under 35 U.S.C. 154(b) by 126 days.

(21) Appl. No.: 18/778,002

(22) Filed: Jul. 19, 2024

(65) Prior Publication Data

US 2025/0025202 A1 Jan. 23, 2025

Related U.S. Application Data

(60) Provisional application No. 63/527,945, filed on Jul. 20, 2023.

(51) Int. Cl.

*A61B 17/3207* (2006.01)
*A61B 17/00* (2006.01)
*A61B 17/32* (2006.01)
*A61B 17/3211* (2006.01)

(52) U.S. Cl.

CPC ................. *A61B 17/320708* (2013.01); *A61B 2017/00371* (2013.01); *A61B 2017/320044* (2013.01); *A61B 2017/32113* (2013.01); *A61B 2217/005* (2013.01)

(58) Field of Classification Search

CPC ................ A61B 17/16; A61B 17/1617; A61B 17/320708; A61B 17/3211; A61B 2017/00353; A61B 2017/00371; A61B 2017/00398; A61B 2017/320044; A61B 2017/32113; A61B 2217/005

USPC .......................................................... 606/160

See application file for complete search history.

(56) References Cited

U.S. PATENT DOCUMENTS

| | | | | | |
|---|---|---|---|---|---|
| 5,961,441 | A * | 10/1999 | Plumb | A61B 1/018 | 600/20 |
| 2010/0057078 | A1* | 3/2010 | Arts | A61B 18/24 | 606/1 |
| 2010/0069922 | A1* | 3/2010 | Kaufman | A61B 17/0467 | 606/138 |
| 2010/0312102 | A1* | 12/2010 | Barnes | A61B 17/3211 | 600/424 |
| 2012/0231416 | A1* | 9/2012 | Drapeau | A61C 3/00 | 2/48 |
| 2015/0157357 | A1* | 6/2015 | Bennett | A61B 17/320708 | 606/131 |
| 2017/0196573 | A1* | 7/2017 | Smith | A61B 17/1633 | |
| 2018/0000526 | A1* | 1/2018 | O'Neil | A61B 50/20 | |
| 2020/0330702 | A1* | 10/2020 | Wilsey | A61B 17/3472 | |

(Continued)

*Primary Examiner* — Jocelin C Tanner

(74) *Attorney, Agent, or Firm* — Kermit D. Lopez; Luis M. Ortiz

(57) ABSTRACT

A surgical apparatus can include a central body that houses a group of different surgical instruments, wherein each surgical instrument among the group of different surgical instruments retracts or deploys from a respective pathway within the central body. The surgical apparatus can also include one or more buttons among a group of buttons located on a thumb side of the central body, such that a surgical instrument among the different surgical instruments can deploy from the respective pathway or retracts back into the respective pathway within the central body in response to a respective push or retraction of the one or more buttons.

27 Claims, 4 Drawing Sheets

(56) References Cited

U.S. PATENT DOCUMENTS

| | | | | |
|---|---|---|---|---|
| 2022/0218187 | A1* | 7/2022 | Bendory | A61B 1/0676 |
| 2024/0423621 | A1* | 12/2024 | Berman | A61B 17/083 |

* cited by examiner

SURGICAL APPARATUS

CROSS REFERENCE TO PROVISIONAL APPLICATION

This patent application claims priority under 35 U.S.C. § 119 to U.S. Provisional Patent Application Ser. No. 63/527,945 entitled "Surgical Apparatus," which was filed on Jul. 20, 2023, and is incorporated herein by reference in its entirety.

TECHNICAL FIELD

Embodiments are generally related to surgical instruments. Embodiments also relate to surgical instrumentation that improves patient care intraoperatively and post operatively. Embodiments further relate to a surgical apparatus that includes multiple different surgical instruments within the confines of a single holding device.

BACKGROUND

Surgical instruments are tools specifically designed and manufactured to aid surgeons in performing various medical procedures. These instruments have evolved over centuries, from simple and rudimentary tools to complex and highly specialized devices. The development of surgical instruments has been driven by the need to improve surgical techniques, enhance patient outcomes, and minimize invasiveness.

Historically, surgical instruments were primarily made of stainless steel or other metals due to their durability and ease of sterilization. However, advancements in technology and material sciences have led to the development of instruments made from various materials, including titanium alloys, ceramics, and polymers. These materials offer advantages such as increased strength, reduced weight, and improved biocompatibility.

Surgical procedures are becoming increasingly intricate and demanding, requiring instruments that can provide greater precision and control. Developing newer instruments with improved designs, ergonomics, and functionalities allows surgeons to perform procedures with enhanced accuracy and efficiency, resulting in better patient outcomes.

Minimally invasive techniques have revolutionized modern surgery by reducing patient trauma, minimizing scarring, and accelerating recovery. Advancements in surgical instruments, such as laparoscopic tools and robotic systems, enable surgeons to perform complex procedures through smaller incisions. Developing instruments tailored for minimally invasive surgery allows for safer and more effective procedures.

Surgery encompasses a wide range of medical specialties, each requiring unique instruments designed for specific procedures. For instance, neurosurgery, orthopedics, cardiovascular surgery, and ophthalmology demand specialized instruments tailored to the anatomical structures and surgical techniques involved. Developing newer instruments ensures that surgeons have the appropriate tools to address the specific challenges of their respective fields.

The development of improved surgical instruments contributes to patient safety by reducing the risk of complications and adverse events. For example, instruments with advanced features, such as real-time imaging capabilities or sensors, can provide surgeons with vital information during procedures, helping to avoid critical structures or detect abnormalities. These innovations enhance patient safety and reduce the potential for errors.

With rapid technological advancements, surgical instruments can integrate cutting-edge technologies such as robotics, artificial intelligence, and virtual reality. Robotic-assisted surgery, for instance, allows for greater precision and dexterity, reducing the margin of error. Developing newer instruments that leverage emerging technologies empowers surgeons with advanced capabilities, enhancing the overall quality of care.

Surgical instruments should not only benefit patients but also improve the working conditions and satisfaction of surgeons. Ergonomic designs, reduced instrument weight, and intuitive interfaces can enhance the comfort and ease of use for surgeons during long and complex procedures. This, in turn, may reduce surgeon fatigue, improve concentration, and lead to better surgical outcomes.

The development of newer, improved surgical instruments is crucial to advance the field of surgery. These instruments enhance precision, support minimally invasive techniques, cater to specialized procedures, promote patient safety, incorporate technological advancements, and improve surgeon comfort. By continually refining surgical instruments, medical professionals can push the boundaries of surgical capabilities and improve patient care.

BRIEF SUMMARY

The following summary is provided to facilitate an understanding of some of the features of the disclosed embodiments and is not intended to be a full description. A full appreciation of the various aspects of the embodiments disclosed herein can be gained by taking the specification, claims, drawings, and abstract as a whole.

It is, therefore, one aspect of the embodiments to provide for an improved surgical apparatus.

It is another aspect of the embodiments to provide for surgical instrumentation that can improve patient care intraoperatively and post operatively.

It is also an aspect of the embodiment to provide for a surgical apparatus that includes multiple different surgical instruments within the confines of a single holding device.

The aforementioned aspects and other objectives can now be achieved as described herein. In an embodiment, a surgical apparatus can include a central body that houses a plurality of different surgical instruments, wherein each surgical instrument among the plurality of different surgical instruments retracts or deploys from a respective pathway within the central body. The surgical apparatus can further include at least one button among a plurality of buttons located on a thumb side of the central body, wherein a surgical instrument among the plurality of different surgical instruments deploys from the respective pathway or retracts back into the respective pathway within the central body in response to a respective push or retraction of the at least one button.

In an embodiment, a width of the surgical apparatus can be based on the contents contained within the surgical apparatus.

An embodiment can further include a battery-powered motor or wifi capability that powers an actuator that actuates a deployment or a retraction of a surgical instrument among the plurality of surgical instruments in response to pressing of the at least one button.

In an embodiment can further include an indentation and a rubber portion configured on the central body, which are usable by a thumb and index finger to assist in manipulating the surgical apparatus.

In an embodiment, the central body can comprise a tubular shaped housing within which the plurality of different surgical instruments are maintained and move within respective pathways associated with each surgical instrument among the plurality of surgical instruments.

In an embodiment, the plurality of different surgical instruments can comprise at least one penfield dissector.

In an embodiment, at least one penfield dissector can comprise at least one of: a #1 penfield dissector, a #2 penfield dissector, and/or a #4 penfield dissector.

In an embodiment, the plurality of different surgical instruments can include at least one curette.

In an embodiment, the at least one curette can comprise at least one of: a 2-0 mm curette, a 3-0 mm curette, and/or a 4-0 mm curette.

In an embodiment, the plurality of different surgical instruments can include at least one scalpel.

In an embodiment, the at least one scalpel can include at least one of: a ten blade scalpel, an eleven blade scalpel, and/or a fifteen blade scalpel.

In an embodiment, the plurality of different surgical instruments can include at least one nerve hook, wherein the at least one nerve hook comprises at least one of a macro nerve hook and/or a microscopic nerve hook.

In an embodiment, the plurality of different surgical instruments can include at least one suction.

In an embodiment, the plurality of different surgical instruments can include a plurality of suctions of different sizes with sizes of at least one of, for example, 6 French, 8 French, and/or 10 French.

In an embodiment the at least one suction is attachable to a standard hospital suction cannister at a superior most portion of the surgical apparatus.

In an embodiment, the plurality of different surgical instruments can include at least one bony drill.

In an embodiment, the plurality of different surgical instruments comprises a plurality of bony drills.

In an embodiment, the plurality of bony drills can include at least three bony drills of varying sizes including at least one of: a 2 mm size, a 3 mm size, and/or a 4 mm size.

In an embodiment, the plurality of different surgical instruments can include at least two surgical instruments selected from among the following different types of surgical instruments: penfield dissector; a nerve hook; a scalpel; a suction; a Kerosene rongeur; a curette; a woodson; and a bony drill.

In an embodiment, the central body can include a working end through which a surgical instrument among the plurality of different surgical instruments can be deployed.

In an embodiment, the working end can include at least one joint that allows for the surgical instrument ejected to change or mold to a desired angle, size or length.

In an embodiment, a working end instrument among the plurality of different surgical instruments can change in angular increments in response to a manipulation of the at least one button located on a thumb side of the central body.

In an embodiment, the angular increments can include at least one of 20 degrees, 40 degrees and/or 90 degrees.

In an embodiment, the working end instrument can change in curved increments in response to a manipulation of the at least one button located on the thumb side of the central body.

In an embodiment, the curved increments are associated with standard currettes of at least one of, for example, 2-0 mm, 3-0 mm, and/or 4-0 mm.

In an embodiment, the working end instrument can change in length in response to a manipulation of the at least one button located on the thumb side of the central body.

In an embodiment, the changes in length of the working end instrument can vary in lengths from 3 mm, 5 mm, and 8 mm with respect to surgical instruments among the plurality of surgical instruments, comprising at least one of: a woodson and a nerve hook.

In an embodiment, the central body and the plurality of different surgical instruments can be sterilized and packaged prior to a surgical use of the surgical apparatus.

BRIEF DESCRIPTION OF THE DRAWINGS

The accompanying figures, in which like reference numerals refer to identical or functionally similar elements throughout the separate views and which are incorporated in and form a part of the specification, further illustrate the embodiments and, together with the detailed description, serve to explain the principles of the embodiments.

Identical or similar parts or elements in the figures may be indicated by the same reference numerals.

DETAILED DESCRIPTION

Figure 1:
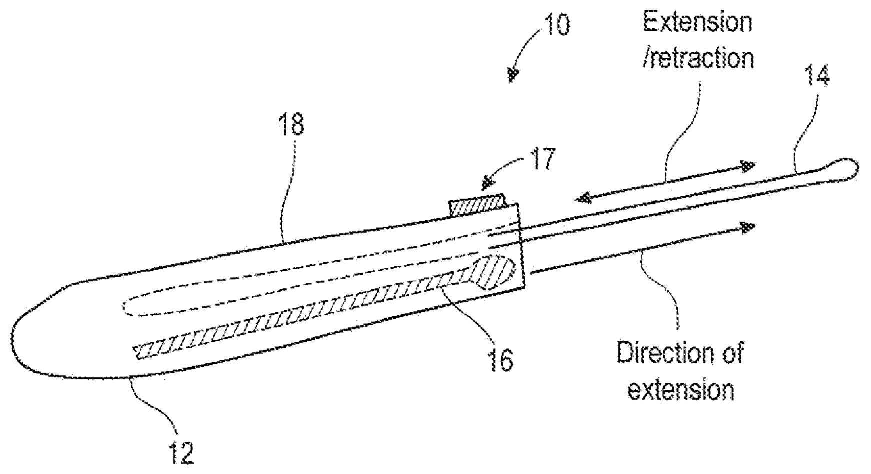
FIG. 1 illustrates a diagram depicting a surgical apparatus, which can be implemented in accordance with an embodiment.

The particular values and configurations discussed in these non-limiting examples can be varied and are cited merely to illustrate one or more embodiments and are not intended to limit the scope thereof.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other issues, subject matter may be embodied as methods, devices, components, or systems. Accordingly, embodiments may, for example, take the form of hardware, software, firmware, or a combination thereof. The following detailed description is, therefore, not intended to be interpreted in a limiting sense.

Throughout the specification and claims, terms may have nuanced meanings suggested or implied in context beyond an explicitly stated meaning. Likewise, phrases such as "in an embodiment" or "in one embodiment" or "in an example embodiment" and variations thereof as utilized herein may or may not necessarily refer to the same embodiment and the phrase "in another embodiment" or "in another example embodiment" and variations thereof as utilized herein may or may not necessarily refer to a different embodiment. It is intended, for example, that claimed subject matter include combinations of example embodiments in whole or in part.

In general, terminology may be understood, at least in part, from usage in context. For example, terms such as "and," "or," or "and/or" as used herein may include a variety of meanings that may depend, at least in part, upon the context in which such terms are used. Generally, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures, or characteristics in a plural sense. Similarly, terms such as "a," "an," or "the", again, may be understood to convey a singular usage or to convey a plural usage, depending at least in part upon context. Furthermore, the term "at least one" as used herein, may refer to "one or more." For example, "at least one widget" may refer to "one or more widgets."

In addition, the term "based on" may be understood as not necessarily intended to convey an exclusive set of factors and may, instead, allow for existence of additional factors not necessarily expressly described, again, depending at least in part on context.

FIG. 1 illustrates a diagram depicting a surgical apparatus 10, which can be implemented in accordance with an embodiment. The surgical apparatus 10 can include a central body 12 that can house a group of different surgical instruments such as, for example, a surgical instrument 14 and a surgical instrument 16. It should be appreciated that although only two surgical instruments 14 and 16 are shown with respect to the embodiment depicted in FIG. 1, more than two surgical instruments may be implemented in accordance with other embodiments of the surgical apparatus 10. Note that the width of the surgical apparatus 10 may depends on the contents of the surgical apparatus 10. For example, the surgical instruments 14 and 16 may be of a particular size and shape and therefore the width of the surgical apparatus 10 may depend on the size and shape of the surgical instruments 14 and 16.

Each surgical instrument (e.g., surgical instrument 14 or surgical instrument 16) among the group of different surgical instruments can retract or deploy from a respective pathway within the central body 12. One or more buttons such as button 17 among a group of buttons can be located on a thumb side 18 of the central body 12, such that one of the surgical instruments 14 or 16 among the group of different surgical instruments can deploy from the respective pathway or retracts back into the respective pathway within the central body 12 in response to a respective push or retraction of the one or more button(s) 17.

The central body 12 can comprise a tubular shaped housing within which the different surgical instruments such as surgical instruments 14, 16, etc., can be maintained and move within respective pathways associated with each of the .surgical instruments 14, 16, etc. It should be appreciated that the central body 12 and the plurality of different surgical instruments 14, 16, etc., can be sterilized and packaged prior to a surgical use of the surgical apparatus 10.

Note that in some embodiments of the surgical apparatus 10, the central body 12 may include a working end through which the surgical instruments 14 or 16 among the plurality of different surgical instruments can be deployed. This working end may include one or more joints that can allow for the surgical instrument 14 or 16 that is ejected to change or mold to a desired angle, size or length. A working end instrument among the different types of surgical instruments maintained with the central body 12 of the surgical apparatus 10 may also change in angular increments in response to a manipulation of at least one of the button(s) 17 located on the thumb side 18 of the central body 12. In an embodiment, these angular increments can include one or more of, for example, 20 degrees, 40 degrees and/or 90 degrees.

In some embodiments, the working end instrument can change in curved increments in response to a manipulation of the button(s) 17 located on the thumb side 18 of the central body 12. These curved increments may be associated with standard currettes of, for example, 2-0 mm, 3-0 mm, and/or 4-0 mm. In addition, the working end instrument may change in length in response to a manipulation of the at button(s) 17 located on the thumb side 18 of the central body 12. The changes in length of the working end instrument can vary in lengths from, for example, 3 mm, 5 mm, and 8 mm with respect to surgical instruments among the group of surgical instruments, such as, for example: a woodson and/or a nerve hook.

The surgical apparatus 10 may be configured from an 'eco-friendly' recyclable biodegradable substance (e.g., any of the following can all work: plastic, carbon fiber, etc.). It is important to note, however, that regardless of the type of material used to configure the surgical apparatus 10, it is preferred to use keep the same length of surgical instruments for the main central holder, or central body 12 of the surgical apparatus 10, with the main working ends of the various currently used surgical instrument(s) deploy from conveniently placed two to three buttons (e.g., 2 buttons if only 2 instruments are within the holder, 3 buttons if 3 instruments are within the holder). Hitting the button 17 once deploys a surgical instrument such as surgical instrument 14 or 16 and hitting the button 17 again retracts the instruments or hitting another button 14 or 16 would retract the surgical instrument and deploy another. It should be appreciated that the above describes just one possible embodiments and scenario of use. Other scenarios and embodiments may be implemented which are different from what has just been described.

Figure 2:
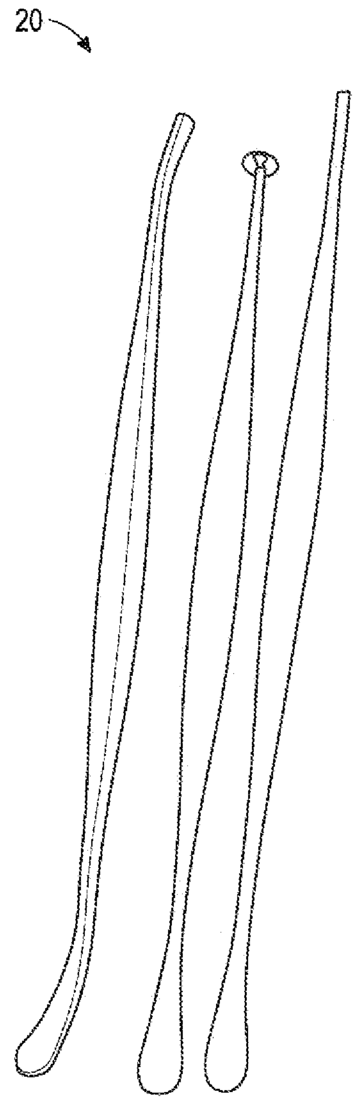
FIG. 2 illustrates an image of example surgical instruments, which may be housed within the surgical apparatus shown in FIG. 1 in accordance with an embodiment.
Figure 3:
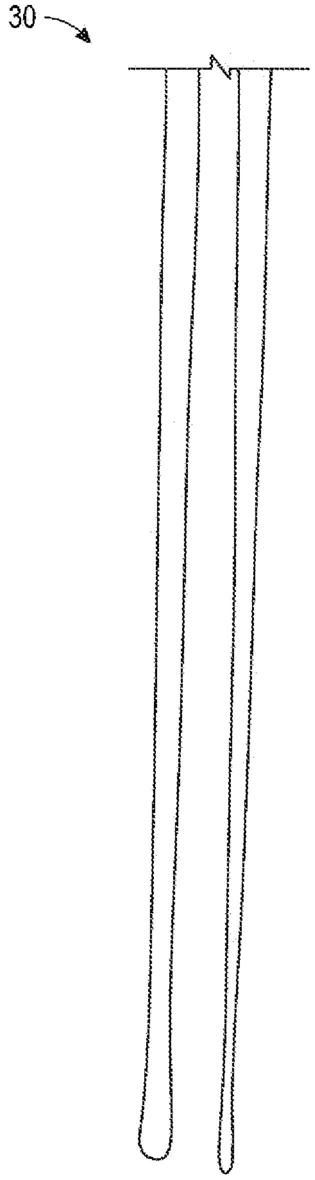
FIG. 3 illustrates an image of other surgical instruments, which may be housed within the surgical apparatus shown in FIG. 1 in accordance with an embodiment.
Figure 4:
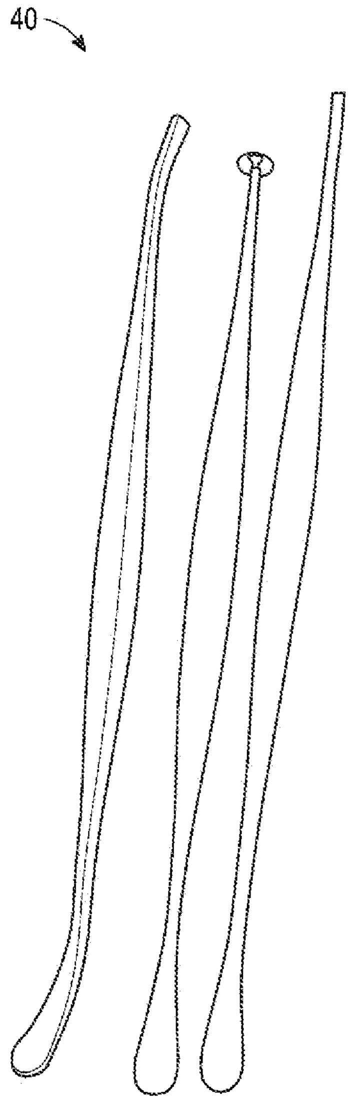
FIG. 4 illustrates an image of a different set of surgical instruments, which may be housed within the surgical apparatus shown in FIG. 1 in accordance with an embodiment.

FIG. 2, FIG. 3, and FIG. 4 illustrates examples of surgical instruments, which may be housed within the surgical apparatus 10 shown in FIG. 1 in accordance with varying embodiments. For example, FIG. 2 illustrates a view of a group of surgical instruments 20. FIG. 3 illustrates a view of a group of surgical instruments 30. FIG. 4 illustrates a view of a group of surgical instruments 40.

It should be appreciated that the particular types of surgical instruments shown in FIGS. 2-4 are presented herein for illustrative purposes only and are not limiting features of the embodiments. That is, other types of surgical instruments may be housed within surgical apparatus 10 in alternative embodiments.

Examples of surgical instruments that can be used to implement the different types of surgical instruments housed with the surgical apparatus 10 include, for example, one or more penfield dissectors, such as, but not limited to a #1 penfield dissector, a #2 penfield dissector, and/or a #4 penfield dissector. Other types of surgical instruments used as part of the different types of surgical instruments for surgical apparatus 10 include, one or more curettes, such as, for example, a 2-0 mm curette, a 3-0 mm curette, and/or a 4-0 mm curette.

The term "penfield dissector" or "Penfield dissector" as utilized herein can relate to a surgical instrument known as a Penfield elevator or Penfield probe, which is commonly used in neurosurgery. It is named after the renowned Canadian neurosurgeon Wilder Penfield, who played a crucial role in its development. The instrument is designed to gently lift and separate delicate neural tissues during brain surgery.

A Penfield dissector typically can possess a long, thin, and flat or slightly curved shape with a smooth, rounded tip. It is usually made of stainless steel or another surgical-grade material to ensure sterility and durability. The length and shape of the dissector allow it to reach deep into the brain while minimizing the risk of damaging surrounding structures. In surgery, the Penfield dissector can be utilized for various purposes. For example, a primary function of the Penfield dissector is to create a safe path through the brain tissue by gently separating and elevating neural structures. This can enable neurosurgeons to access the targeted area of interest without causing unnecessary trauma to adjacent brain regions.

During brain surgery, it is vital for a surgeon to identify and differentiate various brain structures, such as blood vessels, nerves, and tumors. The Penfield dissector helps in this process by gently probing the area and providing tactile feedback to the surgeon. In some cases, the dissector can also aid in achieving hemostasis, which is the control of bleeding during surgery. The rounded tip can be used to apply gentle pressure on bleeding vessels to stop or reduce bleeding. For tumor removal, the Penfield dissector assists in the careful separation of the tumor from surrounding healthy brain tissue, minimizing the risk of damage to critical areas responsible for essential functions. In functional neurosurgery, such as deep brain stimulation (DBS) procedures, the Penfield dissector can be used to implant electrodes or probes into specific brain areas to modulate neural activity and alleviate neurological disorders.

The term "curette" as utilized herein and in the context of surgical instruments, can relate to a handheld surgical tool used for scraping or debriding tissue surfaces. It is a versatile instrument commonly employed in various medical specialties, including general surgery, dermatology, gynecology, orthopedics, and more. Curettes are available in different shapes and sizes, each suited for specific medical procedures.

The typical design of a curette can include a long, slender handle with a rounded, scoop-like working end. The working end may have a smooth, sharp edge, or it may be serrated or have a loop-shaped configuration. The specific design of the curette depends on its intended use and the type of tissue it is meant to scrape or remove.

Curettes serve several purposes in surgery, such as, for example, removing damaged or necrotic tissue, debris, or foreign material from wounds or ulcers. This process can help promote wound healing and reduces the risk of infection. In dermatology or gynecology, curettes can be used to perform biopsies by scraping off a small tissue sample for examination under a microscope to diagnose various skin conditions or cervical abnormalities. In gynecology and gastrointestinal endoscopy, loop curettes may be used to remove polyps or abnormal tissue growths. In orthopedics, bone curettes can be used to scoop out infected or damaged bone tissue in procedures like bone grafting or treatment of bone cysts. In dentistry, curettes can be implemented as dental instruments used for scaling and cleaning the teeth by removing plaque and tartar.

Curettes may be provided in single-use disposable versions for certain applications and also in reusable forms, which are sterilized between uses. Proper care and sterilization protocols are essential to maintain the efficacy and safety of reusable curettes. Overall, curettes play a crucial role in surgical and medical settings by facilitating tissue debridement, biopsy, and other procedures that contribute to patient care and management.

Other examples of surgical instruments can be adapted for use with the surgical apparatus 10 include one or more scalpels such as, for examples, a ten blade scalpel, an eleven blade scalpel, and/or a fifteen blade scalpel.

Further examples of surgical instruments can be adapted for use with the surgical apparatus 10 include one or more nerve hooks, such as one or more of a macro nerve hook and/or a microscopic nerve hook. Note that the term 'nerve hook' as utilized herein can relate to a surgical instrument that can be used to gently lift and manipulate nerves during various surgical procedures. A nerve hook is designed to be a delicate tool with a small, curved or J-shaped hook at the end. The nerve hook allows surgeons to handle nerves with care and precision, minimizing the risk of damage while providing better visibility and access to the surgical site.

The nerve hook is commonly employed in surgeries involving nerves, such as neurosurgery, plastic surgery, orthopedic surgery, and hand surgery. It can be used for several purposes including, for example, helping to expose and isolate the targeted nerve, thereby making it easier for the surgeon to work around it without causing unnecessary trauma. In conditions where nerves are compressed or entrapped, such as carpal tunnel syndrome, the nerve hook can be used to release the pressure and alleviate symptoms. During nerve repair surgeries, such as in cases of nerve lacerations or injuries, the nerve hook assists in aligning the nerve ends and facilitating precise suturing. In situations where a segment of a damaged nerve needs replacement, the nerve hook helps in handling nerve grafts and connecting them to restore nerve continuity.

A microscope nerve hook is a specialized type of nerve hook designed for surgeries that require enhanced visualization using a surgical microscope. These hooks are typically smaller and more delicate than regular nerve hooks, allowing for finer and more precise manipulation of nerves under high magnification. Microscope nerve hooks are commonly used in delicate and intricate surgeries, such as microsurgical procedures for nerve repair, nerve tumor removal, and nerve reconstruction. The use of a surgical microscope provides the surgeon with an enhanced view of the surgical field, allowing them to work with greater precision and accuracy.

The combination of a microscope nerve hook and a surgical microscope can enable neurosurgeons and other specialized surgeons to perform highly intricate procedures with improved outcomes. These instruments play a crucial role in preserving nerve function and improving patients' quality of life after surgery.

A suction is another type surgical instrument that can be adapted for use with the surgical apparatus 10. For examples, suctions of different sizes may be used as one or more of the aforementioned surgical instruments with such sizes including, for example, 6 French, 8 French, and/or 10 French. In some embodiments, a suction used as a surgical instrument for the surgical apparatus 10 may be attachable to a standard hospital suction cannister at a superior most portion of the surgical apparatus.

Note that the term "French" as used herein in the context of surgical instruments, refers to a unit of measurement used to determine the size of certain medical devices, particularly catheters and some other tubular instruments. The French scale, denoted as "Fr," is a numerical scale widely used in the medical field to specify the outer diameter or circumference of these instruments. One French (1 Fr) is equal to ⅓ of a millimeter (0.33 mm) in diameter.

Therefore, as the French size increases, so does the diameter of the instrument. For example:

A 6 Fr catheter has an outer diameter of approximately 2.0 mm.

A 12 Fr catheter has an outer diameter of approximately 4.0 mm.

A 24 Fr catheter has an outer diameter of approximately 8.0 mm.

The French sizing system is important because it helps medical professionals select the appropriate size of the instrument based on the specific medical condition or procedure. For example, in urology, French sizes are used to determine the appropriate size of urinary catheters. In cardiology, French sizes are used to specify the diameter of various cardiovascular catheters, guiding their use during procedures like angiography or angioplasty.

It is worth noting that not all surgical instruments use the French sizing system. Some instruments, such as surgical scissors, forceps, or needle holders, are typically sized differently, using standard measurements or other specialized scales based on their intended use and design.

Other types of surgical instruments that can be used as, for example, the surgical instruments 15 and/16 include one or more bony drills or a group of such bony drills with varying sizes such as, for example, one or more of a 2 mm size, a 3 mm size, and/or a 4 mm size.

A group of surgical instruments used with the surgical apparatus 10 may include two or more surgical instruments selected from among the following different types of surgical instruments: penfield dissector; a nerve hook; a scalpel; a suction; a Kerosene rongeur; a curette; a woodson; and a bony drill.

The following is an example of one possible embodiment of the surgical apparatus 10 with one or more of the following surgical instruments:

a) Penfield 1,2, and 4
b) Macro and microscopic Nerve hooks (angled 20 degree, 30 degree, 90 degree)
c) Scalpel: 10 blade, 11 blade, 15 blade
d) Syringes: with 3 different sizes of needles (18 gauge, 20 gauge, 25 gauge)
e) Bony drill: different sized drill bits The surgical apparatus 100 can thus be configured to house and deploy multiple surgical instruments within the central body 12. The apparatus 100 can include pathways for instruments like surgical instruments 14 and 16, which can be retracted or deployed using buttons 17 on the thumb side 18 of the central body. The central body 12 can be tubular in shape and can contain various surgical instruments, allowing for sterilization and packaging before use.

The apparatus 100 also can feature a working end where instruments can be deployed. This end may include joints enabling the instruments to adjust in angle, size, or length, responding to button manipulations on the central body. Angular adjustments can be in increments such as 20, 40, or 90 degrees, while curved adjustments correspond to standard currette sizes (e.g., 2-0 mm, 3-0 mm, and 4-0 mm). Length adjustments can range from 3 mm to 8 mm, depending on the type of instrument, such as a woodson or nerve hook. As noted previously, the apparatus 100 can be constructed in some embodiments from eco-friendly recyclable biodegradable materials (e.g., plastic, carbon fiber), the apparatus maintains the same instrument length for ease of use. Buttons allow for the deployment and retraction of instruments, with configurations varying based on the number of instruments housed.

Based on the foregoing, it can be appreciated that a number of different embodiments are disclosed herein. For example, in an embodiment, a surgical apparatus can include a central body that houses a plurality of different surgical instruments, wherein each surgical instrument among the plurality of different surgical instruments retracts or deploys from a respective pathway within the central body. The surgical apparatus can further include at least one button among a plurality of buttons located on a thumb side of the central body, wherein a surgical instrument among the plurality of different surgical instruments deploys from the respective pathway or retracts back into the respective pathway within the central body in response to a respective push or retraction of the at least one button.

In an embodiment, a width of the surgical apparatus can be based on the contents contained within the surgical apparatus.

An embodiment can further include a battery-powered motor or wifi capability that powers an actuator that actuates a deployment or a retraction of a surgical instrument among the plurality of surgical instruments in response to pressing of the at least one button.

In an embodiment can further include an indentation and a rubber portion configured on the central body, which are usable by a thumb and index finger to assist in manipulating the surgical apparatus.

In an embodiment, the central body can comprise a tubular shaped housing within which the plurality of different surgical instruments are maintained and move within respective pathways associated with each surgical instrument among the plurality of surgical instruments.

In an embodiment, the plurality of different surgical instruments can comprise at least one penfield dissector.

In an embodiment, at least one penfield dissector can comprise at least one of: a #1 penfield dissector, a #2 penfield dissector, and/or a #4 penfield dissector.

In an embodiment, the plurality of different surgical instruments can include at least one curette.

In an embodiment, the at least one curette can comprise at least one of: a 2-0 mm curette, a 3-0 mm curette, and/or a 4-0 mm curette.

In an embodiment, the plurality of different surgical instruments can include at least one scalpel.

In an embodiment, the at least one scalpel can include at least one of: a ten blade scalpel, an eleven blade scalpel, and/or a fifteen blade scalpel.

In an embodiment, the plurality of different surgical instruments can include at least one nerve hook, wherein the at least one nerve hook comprises at least one of a macro nerve hook and/or a microscopic nerve hook.

In an embodiment, the plurality of different surgical instruments can include at least one suction.

In an embodiment, the plurality of different surgical instruments can include a plurality of suctions of different sizes with sizes of at least one of, for example, 6French, 8 French, and/or 10 French.

In an embodiment the at least one suction is attachable to a standard hospital suction cannister at a superior most portion of the surgical apparatus.

In an embodiment, the plurality of different surgical instruments can include at least one bony drill.

In an embodiment, the plurality of different surgical instruments comprises a plurality of bony drills.

In an embodiment, the plurality of bony drills can include at least three bony drills of varying sizes including at least one of: a 2 mm size, a 3 mm size, and/or a 4 mm size.

In an embodiment, the plurality of different surgical instruments can include at least two surgical instruments selected from among the following different types of surgical instruments: penfield dissector; a nerve hook; a scalpel; a suction; a Kerosene rongeur; a curette; a woodson; and a bony drill.

In an embodiment, the central body can include a working end through which a surgical instrument among the plurality of different surgical instruments can be deployed.

In an embodiment, the working end can include at least one joint that allows for the surgical instrument ejected to change or mold to a desired angle, size or length.

In an embodiment, a working end instrument among the plurality of different surgical instruments can change in angular increments in response to a manipulation of the at least one button located on a thumb side of the central body.

In an embodiment, the angular increments can include at least one of 20 degrees, 40 degrees and/or 90 degrees.

In an embodiment, the working end instrument can change in curved increments in response to a manipulation of the at least one button located on the thumb side of the central body.

In an embodiment, the curved increments are associated with standard curettes of at least one of, for example, 2-0 mm, 3-0 mm, and/or 4-0 mm.

In an embodiment, the working end instrument can change in length in response to a manipulation of the at least one button located on the thumb side of the central body.

In an embodiment, the changes in length of the working end instrument can vary in lengths from 3 mm, 5 mm, and 8 mm with respect to surgical instruments among the plurality of surgical instruments, comprising at least one of: a woodson and a nerve hook.

In an embodiment, the central body and the plurality of different surgical instruments can be sterilized and packaged prior to a surgical use of the surgical apparatus.

The surgical apparatus features a central body housing a variety of surgical instruments, each of which can retract or deploy from respective pathways within the central body. The deployment or retraction can be controlled by buttons located on the thumb side of the body. The apparatus' width can be determined by its contents, and it may include a battery-powered motor or WiFi capability to power the actuator for instrument deployment and retraction. The central body, which is tubular in shape, includes indentations and rubber portions for improved manipulation by the thumb and index finger.

The surgical instruments can encompass a wide range, including at least one penfield dissector (with variations like #1, #2, and #4), curettes (e.g., 2-0 mm, 3-0 mm, 4-0 mm), scalpels (e.g., ten blade, eleven blade, fifteen blade), nerve hooks (macro and microscopic), suctions (attachable to standard hospital suction cannisters), bony drills (with sizes 2 mm, 3 mm, 4 mm), and other types such as Kerosene rongeurs and woodsons. The apparatus allows for changes in the angle, curve, and length of the instruments at the working end, with specific angular increments and curved increments for instruments like curettes, as well as varying lengths for instruments such as woodsons and nerve hooks. Finally, the surgical apparatus can be designed to be sterilized and packaged prior to use.

It will be appreciated that variations of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which are also intended to be encompassed by the following claims.

What is claimed is:

1. A surgical apparatus, comprising:

a central body that houses a plurality of different surgical instruments, wherein each surgical instrument among the plurality of different surgical instruments is configured to retract or deploy from a respective pathway within the central body, the central body including a working end through which a surgical instrument among the plurality of different surgical instruments is configured to be deployed;

at least one button among a plurality of buttons located on a thumb side of the central body, wherein a surgical instrument among the plurality of different surgical instruments is configured to deploy from the respective pathway or retract back into the respective pathway within the central body in response to a respective push or retraction of the at least one button, wherein the working end comprises at least one joint that allows for the surgical instrument to be ejected to change or mold to a desired angle, size or length.

2. The surgical apparatus of claim 1, wherein a width of the surgical apparatus is based on contents contained within the surgical apparatus.

3. The surgical apparatus of claim 1, further comprising a battery-powered motor or wifi capability that is configured to power an actuator that actuates a deployment or a retraction of a surgical instrument among the plurality of surgical instruments in response to pressing of the at least one button.

4. The surgical apparatus of claim 1, further comprising:

an indentation and a rubber portion configured on the central body, wherein a width of the surgical apparatus is based on contents contained within the surgical apparatus.

5. The surgical apparatus of claim 1, further comprising an indentation and a rubber portion configured on the central body, which are usable by a thumb and index finger to assist in manipulating the surgical apparatus.

6. The surgical apparatus of claim 1, wherein the central body comprises a tubular shaped housing within which the plurality of different surgical instruments is maintained and configured to move within respective pathways associated with each surgical instrument among the plurality of surgical instruments.

7. The surgical apparatus of claim 1, wherein the plurality of different surgical instruments comprises at least one penfield dissector.

8. The surgical apparatus of claim 7, wherein the at least one penfield dissector comprises at least one of: a #1 penfield dissector, a #2 penfield dissector, and a #4 penfield dissector.

9. The surgical apparatus of claim 1, wherein the plurality of different surgical instruments comprises at least one curette.

10. The surgical apparatus of claim 9, wherein the at least one curette comprises at least one of: a 2-0 mm curette, a 3-0 mm curette, and a 4-0 mm curette.

11. The surgical apparatus of claim 1, wherein the plurality of different surgical instruments comprises at least one scalpel.

12. The surgical apparatus of claim 11, wherein the at least one scalpel comprises at least one of: a ten blade scalpel, an eleven blade scalpel, and a fifteen blade scalpel.

13. The surgical apparatus of claim 1, wherein the plurality of different surgical instruments comprises at least one nerve hook, wherein the at least one nerve hook comprises at least one of a macro nerve hook and a microscopic nerve hook.

14. The surgical apparatus of claim 1, wherein the plurality of different surgical instruments comprises at least one suction.

15. The surgical apparatus of claim 14, wherein the plurality of different surgical instruments comprises a plurality of suctions of different sizes with sizes of at least one of 6 French, 8 French, and 10 French.

16. The surgical apparatus of claim 14, is wherein the at least one suction is attachable to a standard hospital suction cannister at a superior most portion of the surgical apparatus.

17. The surgical apparatus of claim 1, wherein the plurality of different surgical instruments comprises at least one bony drill.

18. The surgical apparatus of claim 1, wherein the plurality of different surgical instruments comprises a plurality of bony drills.

19. The surgical apparatus of claim 18, wherein the plurality of bony drills comprises at least three bony drills of varying sizes including at least one of: a 2 mm size, a 3 mm size, and a 4 mm size.

20. The surgical apparatus of claim 1, wherein the plurality of different surgical instruments comprises at least two surgical instruments selected from among the following different types of surgical instruments:

penfield dissector;

a nerve hook;

a scalpel;

a suction;

a Kerosene rongeur, a curette;

a woodson; and a bony drill.

21. The surgical apparatus of claim 1, wherein a working end instrument among the plurality of different surgical instruments is configured to change in angular increments in response to a manipulation of the at least one button located on a thumb side of the central body.

22. The surgical apparatus of claim 21, wherein the angular increments comprise at least one of 20 degrees, 40 degrees and 90 degrees.

23. The surgical apparatus of claim 21, wherein the working end instrument is configured to change in curved increments in response to a manipulation of the at least one button located on the thumb side of the central body.

24. The surgical apparatus of claim 23, wherein the curved increments are associated with standard currettes of at least one of: 2-0 mm, 3-0 mm, and 4-0 mm.

25. The surgical apparatus of claim 21, wherein the working end instrument is configured to change in length in response to a manipulation of the at least one button located on the thumb side of the central body.

26. The surgical apparatus of claim 25, wherein the changes in length of the working end instrument varying lengths from 3 mm, 5 mm, and 8 mm with respect to surgical instruments among the plurality of surgical instruments comprises at least one of: a woodson and a nerve hook.

27. The surgical apparatus of claim 1, wherein the central body and the plurality of different surgical instruments are sterilized and packaged prior to a surgical use of the surgical apparatus.

* * * * *